(12) United States Patent
Roeder et al.

(10) Patent No.: US 7,753,948 B2
(45) Date of Patent: Jul. 13, 2010

(54) INTRALUMINAL DEVICE WITH UNSYMMETRIC TAPERED BEAMS

(75) Inventors: Blayne A. Roeder, Lafayette, IN (US); Alan R. Leewood, Lafayette, IN (US)

(73) Assignee: Med Institute Inc., Lafayette, IN (US)

( * ) Notice: Subject to any disclaimer, the term of this patent is extended or adjusted under 35 U.S.C. 154(b) by 319 days.

(21) Appl. No.: 11/455,274

(22) Filed: Jun. 15, 2006

(65) Prior Publication Data

US 2006/0287707 A1 Dec. 21, 2006

Related U.S. Application Data

(60) Provisional application No. 60/690,824, filed on Jun. 15, 2005.

(51) Int. Cl.
*A61F 2/06* (2006.01)
(52) U.S. Cl. .................................................. 623/1.15
(58) Field of Classification Search ........ 623/1.15–1.17
See application file for complete search history.

(56) References Cited

U.S. PATENT DOCUMENTS

| 4,893,623 | A | 1/1990 | Rosenbluth |
| 5,861,027 | A | 1/1999 | Trapp |
| 6,190,406 | B1 | 2/2001 | Duerig et al. ................. 623/1.2 |
| 6,540,774 | B1* | 4/2003 | Cox ............................ 623/1.15 |
| 2001/0032011 | A1* | 10/2001 | Stanford ..................... 623/1.15 |
| 2002/0095140 | A1* | 7/2002 | Lootz et al. ..................... 606/1 |

FOREIGN PATENT DOCUMENTS

WO    WO 0224111    3/2002

OTHER PUBLICATIONS

U.S. Appl. No. 11/454,303, filed Jun. 15, 2006, Roeder et al.
International Search Report and Written Opinion from PCT/US2006/023465, dated Oct. 4, 2006, 11 p.

* cited by examiner

*Primary Examiner*—Corrine M McDermott
*Assistant Examiner*—Rebecca Straszheim
(74) *Attorney, Agent, or Firm*—Brinks Hofer Gilson & Lione

(57) ABSTRACT

A beam is provided for intraluminal devices. The beam is defined by a first side surface and a second side surface. The first side surface is tapered at a different rate than the second side surface. One advantage of the beam is that strain which is normally concentrated in adjacent, interconnected bends is redirected onto the length of the beam. This may increase the fatigue life of intraluminal devices or may be used to fashion new structures with improved performance.

11 Claims, 2 Drawing Sheets

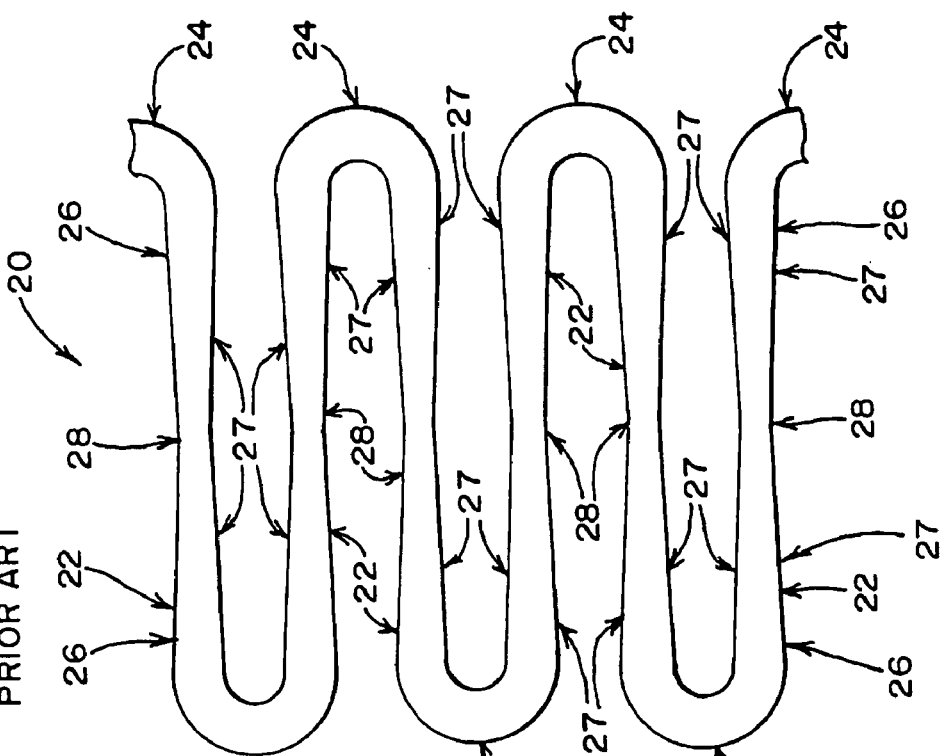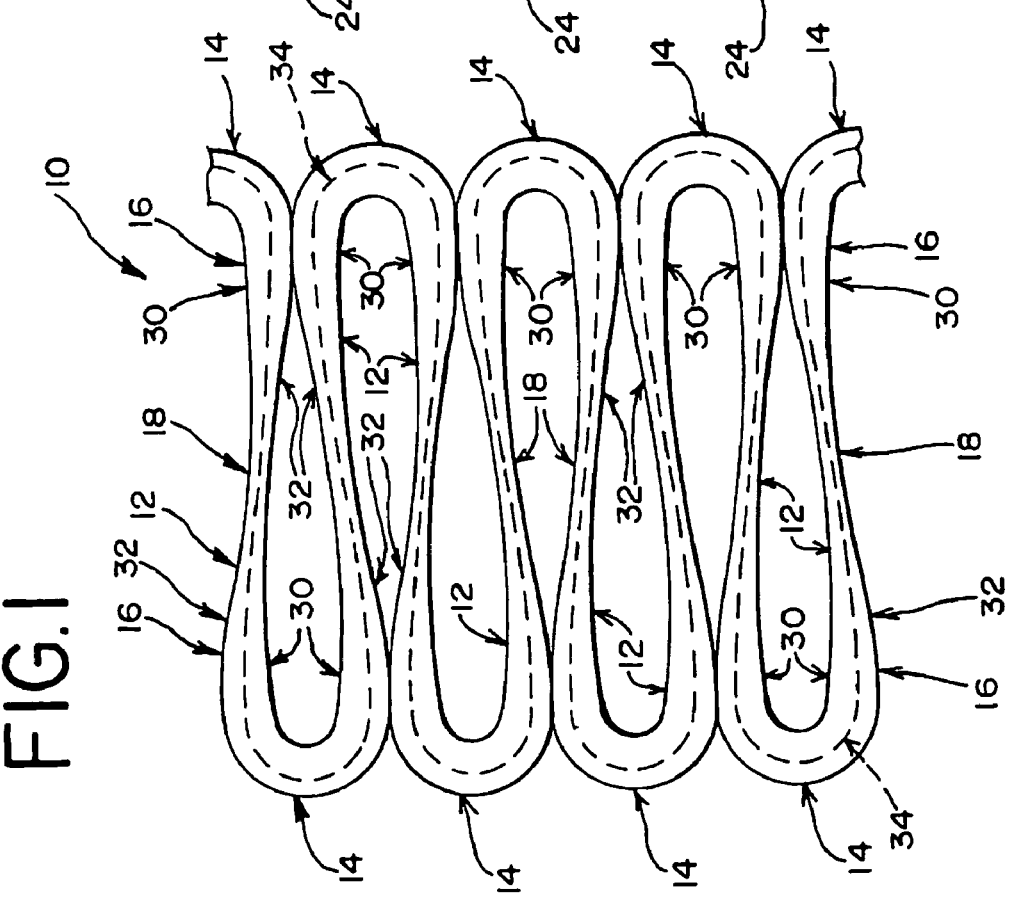

US 7,753,948 B2

INTRALUMINAL DEVICE WITH UNSYMMETRIC TAPERED BEAMS

This application claims priority to U.S. Provisional Application No. 60/690,824, filed Jun. 15, 2005, which is hereby incorporated by reference herein.

RELATED APPLICATIONS

This application is related to U.S. patent application Ser. No. 11/454,303, incorporated herein by reference and entitled Intraluminal Device With Improved Tapered Beams, filed by the same inventors on the same day as the present application.

BACKGROUND

The present invention relates generally to medical devices and more particularly to intraluminal devices suitable for percutaneous transluminal delivery into a body.

A variety of intraluminal devices are known to those in the medical arts, including stents, stent-grafts, filters, occluders, artificial valves and other endoprosthetic devices. For example, stents have now become a relatively common device for treating a number of organs, such as the vascular system, colon, biliary tract, urinary tract, esophagus, trachea and the like. Stents are useful in a variety of medical procedures and are often used to treat blockages, occlusions, narrowing ailments and other related problems that restrict flow through a passageway. Stents are also useful in treating various types of aneurysms, either in the form of a stent-graft or to retain an embolization device within the aneurysm.

The above-described examples are only some of the applications in which intraluminal devices are used by physicians. Many other applications for intraluminal devices are known and/or will be developed in the future. For example, in addition to the use of stents and stent-grafts to treat vascular stenosis and aneurysms, similar procedures may also be used to deploy vascular filters, occluders, artificial valves and other endoprosthetic devices.

Typically, intraluminal devices are made from a series of interconnected beams and bends. The beams and bends are usually made from an elastic material like stainless steel or nitinol. As a result, the intraluminal device may be collapsed into a low profile by flexing the bends. This introduces strain into the bends, which typically causes the intraluminal device to exert radial force. Thus, as the bends are flexed to a greater degree, more strain is introduced and the intraluminal device exerts more radial force.

For example, in the case of a stent, conventional stent structures are made up of interconnected struts and bends that form a cylindrical structure with a longitudinal inner lumen passing therethrough. Various methods are known to those in the art for making such stent structures. For example, stent structures may be made by laser cutting a structure from a cannula. Stents may also be made by braiding wires together to form struts.

In order to deliver a stent through narrow passageways, the stent is typically collapsed into a delivery configuration with a small diameter. The collapsed stent structure may then be inserted into a sheath which retains the stent in the delivery configuration until it is released. Because the stent must be significantly collapsed in this configuration, a large strain is introduced into the stent structure. Since a typical stent structure is only collapsed into the delivery configuration one time or a minimal number of times, it is generally considered that the stent structure can accommodate a large strain level in this application without resulting in permanent damage to the stent structure.

Once the stent is released at the site of implantation, the stent structure expands and contacts the lumen wall. In this process, a large portion of the strain is relieved. However, in most cases it is desirable for the stent to exert at least a minimum radial force against the lumen wall after implantation. Therefore, the size of stent which is usually selected for a particular use has a fully expanded, or relaxed, diameter that is larger than the lumen wall in which the stent will be implanted. As a result, the strain in the stent structure is not completely relieved after implantation, and the stent structure remains permanently under a lower amount of strain.

One problem with current stent structures is that they may weaken and/or fail due to fatigue in the bends that interconnect the struts. Fatigue may occur because stents are frequently implanted into organs like arteries that pulse in diameter each time that the heartbeats. As a result, the stent structure expands and contracts a small amount with each heartbeat. With each expansion and contraction of the stent, the strain in the stent structure cycles between two different strain levels. Over many strain cycles, the structure of the stent may eventually become permanently damaged. One risk is that fatigue damage may cause bends in the stent structure to fracture and break. This may result in undesirable tissue damage and may reduce the effectiveness of the stent. Moreover, fatigue behavior, in addition to considerations of the high initial strain introduced into the stent during delivery, may limit the design choices available to makers of stents. For example, stents with longer struts are sometimes used in order to minimize the strain on the bends. However, stents with longer struts may be subject to undesirable tissue prolapse after implantation, in which tissues of the lumen wall grow around and encapsulate the stent structure. In certain applications, stents with shorter struts may be desirable to minimize tissue prolapse and to increase the radial force exerted on the lumen wall. However, stents with shorter struts may be subject to higher strain levels which may damage the structure of the stent.

BRIEF SUMMARY

A strut, or beam, is described for intraluminal devices. The strut is formed by a first side surface and a second side surface that define a width of the strut. The first side surface and second side surface are tapered so that the width of the strut is wider adjacent a bend and narrower adjacent a middle portion. The rate of taper of the first side surface is also different than the taper of the second side surface. As a result, strain is redistributed away from the adjacent bend and is distributed onto the length of the strut. Additional details and advantages are described below in the detailed description.

The invention may include any of the following aspects in various combinations and may also include any other aspect described below in the written description or in the attached drawings.

An intraluminal device, comprising:

a first beam comprising a first end portion, a second end portion and a middle portion connecting the first end portion and the second end portion;

a first bend connected to the first end portion, the first bend being further connected to a second beam;

a second bend connected to the second end portion, the second bend being further connected to a third beam;

wherein the first bend and the second bend are elastic, the first beam, the second beam and the third beam thereby being collapsible to form a low profile and expandable to form a larger profile;

the first end portion comprising a first side surface disposed toward the first bend and a second side surface disposed away from the first bend; and a first distance between the first side surface and the second side surface adjacent the first bend being greater than a second distance between the first side surface and the second side surface adjacent the middle portion, a width of the first end portion thereby being tapered between the first bend and the middle portion, wherein the first side surface is tapered at a different rate than the second side surface.

The intraluminal device wherein the first beam, the second beam and the third beam comprise struts in a stent, an included angle defined by the struts being adapted to be less than 5° in the low profile.

The intraluminal device wherein the second beam comprises a third end portion corresponding to the first end portion of the first beam, the third end portion being connected to the first bend.

The intraluminal device wherein the first bend and the second bend face in opposite directions, the second end portion comprising a third side surface disposed toward the second bend and a fourth side surface disposed away from the second bend, and the third side surface is tapered at substantially the same rate as the first side surface and the fourth side surface is tapered at substantially the same rate as the second the surface.

The intraluminal device wherein the second beam and the third beam comprise first end portions, second end portions and middle portions corresponding to the first end portion, the second end portion and the middle portion of the first beam.

The intraluminal device wherein a centerline extending through the first end portion, the middle portion and the second end portion forms an S-shape.

The intraluminal device wherein the first side surface is tapered along a concave curve.

The intraluminal device wherein the second side surface is tapered along a convex curve.

The intraluminal device wherein the first bend comprises a first side and an opposing second side, the first side and the second side extending parallel to a longitudinal axis of the stent, the first side and the second side thereby being adapted to abut corresponding sides of matching bends when the first beam, the second beam and the third beam are collapsed, wherein a reinforcement region of the first bend is formed between the first side and the second side.

The intraluminal device further comprising a radial opening extending through the reinforcement region.

The intraluminal device wherein a centerline extending through the first end portion, the middle portion and the second end portion forms an S-shape, and the first side surface is tapered along a concave curve.

The intraluminal device wherein a centerline extending through the first end portion, the middle portion and the second end portion forms an S-shape, and the second side surface is tapered along a convex curve.

The intraluminal device wherein the first side surface is tapered along a concave curve.

The intraluminal device wherein the first bend and the second bend face in opposite directions, the second end portion comprising a third side surface disposed toward the second bend and a fourth side surface disposed away from the second bend, and the third side surface is tapered at substantially the same rate as the first side surface and the fourth side surface is tapered at substantially the same rate as the second the surface, and wherein the second beam and the third beam comprise first end portions, second end portions and middle portions corresponding to the first end portion, the second end portion and the middle portion of the first beam.

The intraluminal device wherein the first beam, the second beam and the third beam comprise struts in a stent, an included angle defined by the struts being adapted to be less than 5° in the low profile.

An intraluminal device, comprising:

a first beam, a second beam and a bend connecting the first beam and the second beam, wherein the bend is elastic, the first beam and the second beam thereby being collapsible to form a low profile and expandable to form a larger profile;

the first beam comprising a first side surface disposed toward the bend and a second side surface disposed away from the bend, a width of the first beam being tapered along a first portion of the first beam, wherein the first side surface is tapered at a different rate than the second side surface; and the second beam comprising a third side surface disposed toward the bend and a fourth side surface disposed away from the bend, a width of the second beam being tapered along a second portion of the second beam, wherein the third side surface is tapered at a different rate than the fourth side surface.

The intraluminal device wherein the first beam and the second beam comprise struts in a stent, an included angle defined by the struts being adapted to be less than 5° in the low profile.

The intraluminal device wherein the third side surface is tapered at substantially the same rate as the first side surface and the fourth side surface is tapered at substantially the same rate as the second side surface.

The intraluminal device wherein a first centerline extending through the first portion and a second centerline extending through the second portion form S-shapes.

The intraluminal device wherein the first side surface and the third side surface are tapered along concave curves.

The intraluminal device wherein the second side surface and the fourth side surface are tapered along convex curves.

The intraluminal device wherein a first centerline extending through the first portion and a second centerline extending through the second portion form S-shapes, and the first side surface and the third side surface are tapered along concave curves.

The intraluminal device wherein a first centerline extending through the first portion and a second centerline extending through the second portion form S-shapes, and the second side surface and the fourth side surface are tapered along convex curves.

The intraluminal device wherein the first side surface and the third side surface are tapered along concave curves.

The intraluminal device wherein the third side surface is tapered at substantially the same rate as the first side surface and the fourth side surface is tapered at substantially the same rate as the second side surface.

The intraluminal device wherein the first beam and the second beam comprise struts in a stent, an included angle defined by the struts being adapted to be less than 5° in the low profile.

BRIEF DESCRIPTION OF SEVERAL VIEWS OF THE DRAWINGS

The invention may be more fully understood by reading the following description in conjunction with the drawings, in which:

FIG. 1 is a plan view of an improved stent structure;

FIG. 2 is a plan view of a prior art stent structure;

DETAILED DESCRIPTION

Figure 3:
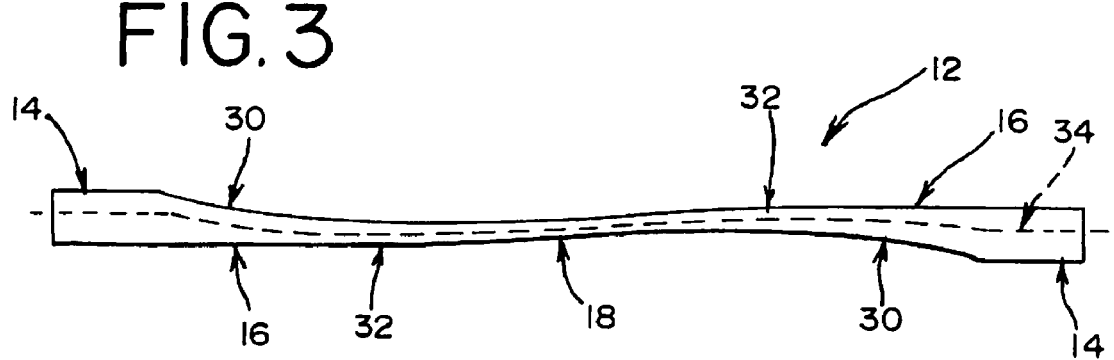
FIG. 3 is a plan view of a strut shown in FIG. 1.

Referring now to the figures, and particularly to FIG. 1, an improved stent structure 10 is shown. The stent structure 10 includes a series of struts 12, or beams 12, interconnected by a series of bends 14. Preferably, the stent structure 10 is made from an elastic material like nitinol or stainless steel. The stent structure 10 may be made by conventional manufacturing techniques, such as laser cutting the structure from a metal cannula or other known methods. As shown in FIG. 1, each strut 12 is formed from two end portions 16 that are connected together by a middle portion 18. Each end portion 16 of the struts 12 is further connected to a bend 14 which is connected on each side to different struts 12. The bends 14 on opposing ends of each strut 12 face in opposite directions. Thus, the bends 14 interconnect together the series of struts 12 to form a stent structure 10. The bends 14 and struts 12 may also be further connected to other struts and bends or other structures to form the desired length, diameter and geometry of a stent. The stent structure 10 shown in FIG. 1 is only one example of the type of stent structure that may be used, and many different stent structures or other structures for intraluminal devices may be formed using the struts 12, or beams 12, described herein. In FIG. 1, a typical stent structure 10 that is well known to those in the art is shown in a collapsed, low profile configuration. In the low profile configuration the included angle between adjacent struts 12 is normally less than 5°. This configuration would typically be used to thread the stent structure 10 through intravascular passageways to position the stent for implantation at a desired area for treatment. Typically, at the site of implantation the stent is released, and the stent structure 10 expands to a large profile until the stent contacts the artery wall or other tissue structure.

Figure 4:
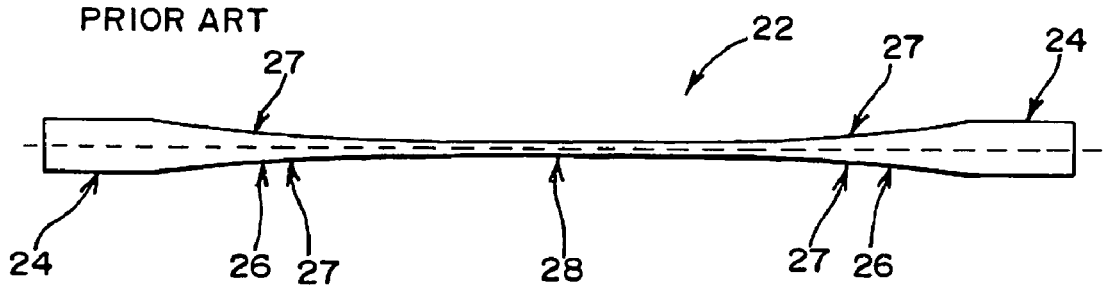
FIG. 4 is a plan view of a prior art strut shown in FIG. 2.

In order to compress the stent structure 10 into the low profile configuration shown in FIG. 1, a relatively large strain must be introduced into the stent structure 10. However, in conventional stent structures the strain which is introduced into the stent structure is typically concentrated in the bends of the structure. Because of this problem, the designs of most conventional stents are limited in the range of expansion and compression that the stent can achieve, the length of struts that may be used, and/or other design considerations. In FIG. 2, one prior art stent structure 20 is shown. This prior art stent structure 20 is described in U.S. Pat. No. 6,190,406 to Duerig et al. A single strut 22 of the prior art stent structure 20 is shown in FIG. 4. As shown in FIG. 2, the prior art stent structure 20 has a series of struts 22 that are interconnected by a series of bends 24. Each strut 22 is formed by two end portions 26 connected together by a middle portion 28. As shown, the end portions 26 are tapered toward each middle portion 28 so that the width of the end portions 26 is wider adjacent the bends 24 and is narrower adjacent the middle portion 28. As shown in FIG. 2 herein and described in Duerig et al., the taper of the end portions 26 may be a simple linear tapered reduction in width. Moreover, as shown in the figures of Duerig et al., both side surfaces 27 of the end portions 26 are tapered at the same rate as each other. As descried in Duerig et al., the bending radius is kept constant in this design, and the bending of the end portions 26 is defined by the formula $1/R=12FLI(ETW^3)$. Duerig et al. concludes that the strut width should vary as the cube root of the distance from the end.

Conventional stent structures, including the one shown in FIG. 2, do not achieve the level of strain distribution along the length of the struts that may be achieved with the improved struts 12 shown in FIGS. 1 and 3. Ideally, the strain concentration which is normally experienced at the bends of the stent structure would be distributed away from the bends and shared along the length of each end portion. In this way, the maximum strain levels experienced by conventional stents may be reduced. This may be achieved by redirecting the strain that is normally concentrated in the bends to areas that normally experience minimal strain levels. For example, in FIGS. 1 and 3, the width of each end portion 16 is defined by a first surface 30 facing toward the adjacent bend 14 and a second side surface 32 facing away from the adjacent bend 14. As shown, the end portions 16 are tapered toward each middle portion so that the width of the end portions 16 is wider adjacent the bends 14 and is narrower adjacent the middle portion 18. Preferably, the middle portions 18 are smoothly contoured between two opposing end portions 16. Unlike the prior art, the first side surface 30 is tapered at a different rate than the second side surface 32. For example, as shown, the first side surface 30 may be tapered along a concave curve, and the second side surface 32 may be tapered along a convex curve. Moreover, as further shown, a centerline 34 extending through the middle portion 18 and the two opposing end portions 16 of a strut 12 forms an S-shape. The first side surfaces 30 that face the bends 14 of each end portion 16 may all have the same tapered shape in the stent structure 10 but may also have different tapered shapes as desired. Similarly, the second side surfaces 32 that face away from the bends 14 of each end portion 16 may all have the same tapered shape but may also have different tapered shapes as desired.

One of the advantages of the improved strut 12 is that strain is distributed more evenly throughout the stent structure 10. In particular, strain levels may be redistributed away from the bends 14 and distributed along the length of the struts 12. As a result, the maximum strain levels may be reduced. This may allow designers to optimize the expanded and collapsed diameters of a stent. For example, stent structures may be compressed to smaller collapsed diameters without permanently deforming or damaging the structure of the stent. This may allow stents to be used in smaller passageways and may minimize the trauma of introducing stent delivery systems. Further, stents with wider expansion ratios may be designed to reduce the number of different stents that are needed to treat various conditions. In addition, stents may be designed with shorter struts to minimize tissue prolapse and increase radial force.

Another advantage of the improved struts 12 is that the fatigue life of the stent structure 10 may be increased. Fatigue life may be a concern with traditional stent structures since stents remain slightly compressed by the artery wall or other tissue structure even after implantation. This compression introduces an operational strain into the stent structure.

Because a person's heart typically causes the arteries in the vascular system to expand and contract with each heartbeat, an implanted stent normally expands and contracts a small amount each time the heart beats. In conventional stent structures, this may cause a fatigue failure in the bends of the stent structure since the cycles of operational strain are concentrated in the bends. By contrast, the improved struts 12 may reduce the risk of bend failures by minimizing the operational strain levels. For example, in a comparison of the struts 12, 22 shown in FIGS. 3 and 4, the strut 22 in FIG. 4 has a fatigue margin of 1.50, while the strut shown in FIG. 3 has a fatigue margin of 2.35. Additionally, the strut 12 shown in FIG. 3 also produces approximately 25% more radial force than the strut 22 shown in FIG. 4.

Figure 5:
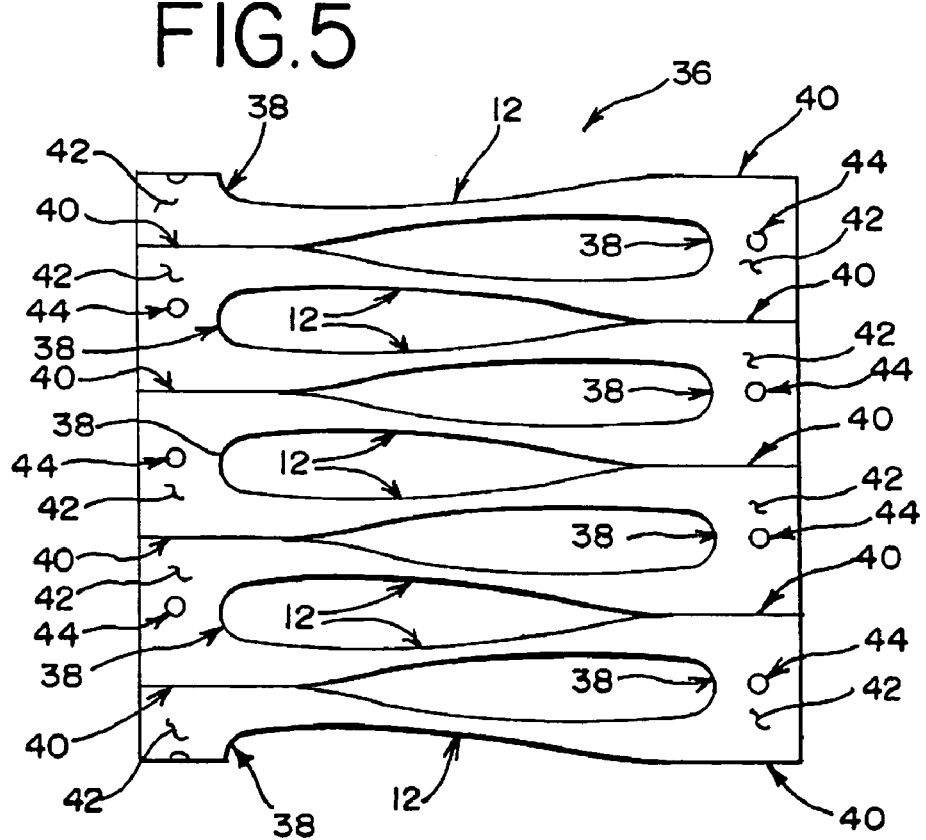
FIG. 5 is a plan view of a stent structure with reinforcement regions along bends of the stent structure.

As shown in FIG. 5, the described strut 12 may also be used in a stent structure 36 in which the bends 38 are formed to abut against each other in the collapsed, low profile configuration. In this embodiment, the bends 38 are formed by opposing side surfaces 40 that extend parallel to the longitudinal axis of the stent. As a result, a reinforcement region 42 is formed between the opposing side surfaces 40 of the bends 38. A radial opening 44 may also extend through the reinforcement region 42, which may be used to retain sutures for a stent-graft or for radiopaque material for a marker.

While preferred embodiments of the invention have been described, it should be understood that the invention is not so limited, and modifications may be made without departing from the invention. The scope of the invention is defined by the appended claims, and all devices that come within the meaning of the claims, either literally or by equivalence, are intended to be embraced therein. Furthermore, the advantages described above are not necessarily the only advantages of the invention, and it is not necessarily expected that all of the described advantages will be achieved with all embodiments of the invention.

We claim:

1. An intraluminal device, comprising:
   a first beam comprising a first end portion, a second end portion and a middle portion connecting said first end portion and said second end portion,
   a first bend connected to said first end portion, said first bend being further connected to a second beam;
   a second bend connected to said second end portion, said second bend being further connected to a third beam;
   wherein said first bend and said second bend are elastic, said first beam, said second beam and said third beam thereby being collapsible to form a low profile and expandable to form a larger profile;
   said first end portion comprising a first side surface disposed toward said first bend and a second side surface disposed away from said first bend, said first and second side surfaces extending over a length of said first beam from said first bend to said middle portion;
   a first distance between said first side surface and said second side surface adjacent said first bend being greater than a second distance between said first side surface and said second side surface adjacent said middle portion, a width of said first end portion thereby being tapered between said first bend and said middle portion, wherein, when in said low profile, said first side surface is tapered along a concave curve at a different rate than said second side surface is tapered along a convex curve; and
   wherein a centerline of said first beam defines an S-shape along the full length of said first beam when said first beam is substantially straightened.

2. The intraluminal device according to claim 1, wherein said first beam, said second beam and said third beam comprise struts in a stent, an included angle defined by said struts being adapted to be less than 5° in said low profile.

3. The intraluminal device according to claim 1, wherein said first bend and said second bend face in opposite directions, said second end portion comprising a third side surface disposed toward said second bend and a fourth side surface disposed away from said second bend, and said third side surface is tapered at substantially the same rate as said first side surface and said fourth side surface is tapered at substantially the same rate as said second said surface, said second beam comprising third and fourth end portions and a second middle portion, said third beam comprising fifth and sixth end portions and a third middle portion, said third and fifth end portions corresponding to said first end portion, said fourth and sixth end portions corresponding to said second end portion and said second and third middle portions corresponding to said middle portion of said first beam.

4. The intraluminal device according to claim 1, wherein said first bend comprises a first opposing side surface and a second opposing side surface, said first opposing side surface and said second opposing side surface extending parallel to a longitudinal axis of said intraluminal device, said first opposing side surface and said second opposing side surface thereby being adapted to abut corresponding opposing side surfaces of matching bends when said first beam, said second beam and said third beam are collapsed, wherein a reinforcement region of said first bend is formed between said first opposing side surface and said second opposing side surface.

5. The intraluminal device according to claim 4, further comprising a radial opening extending through said reinforcement region.

6. An intraluminal device, comprising:
   a first beam, a second beam and a bend connecting said first beam and said second beam, wherein said bend is elastic, said first beam and said second beam thereby being collapsible to form a low profile and expandable to form a larger profile;
   said first beam comprising a first side surface disposed toward said bend and a second side surface disposed away from said bend, said first side surface and said second side surface extending over a part of a length of said first beam from said bend to a middle portion of said first beam, and a width of said first beam being non-constant and tapered along a first portion of said first beam corresponding to said first and second side surfaces, wherein said first side surface is tapered at a different rate than said second side surface, wherein, when in said low profile, said first side surface is tapered over a concave curve and said second surface is tapered over a convex curve;
   said second beam comprising a third side surface disposed toward said bend and a fourth side surface disposed away from said bend, said third side surface and said fourth side surface extending over a part of a length of said second beam from said bend to a middle portion of said second beam, and a width of said second beam being non-constant and tapered along a second portion of said second beam corresponding to said third and fourth side surfaces, wherein said third side surface is tapered at a different rate than said fourth side surface, wherein, when in said low profile, said third side surface is tapered over a concave curve and said fourth surface is tapered over a convex curve; and
   wherein a first centerline of said first beam and a second centerline of said second beam each define S-shapes along the full length of said first and second beams when said first and second beams are substantially straightened.

7. The intraluminal device according to claim 6, wherein said first beam and said second beam comprise struts in a stent, an included angle defined by said struts being adapted to be less than 5° in said low profile.

8. The intraluminal device according to claim 6, wherein said third side surface is tapered at substantially the same rate as said first side surface and said fourth side surface is tapered at substantially the same rate as said second side surface.

9. The intraluminal device according to claim 6, wherein said first beam and said second beam comprise struts in a stent, an included angle defined by said struts being adapted to be less than 5° in said low profile, said third side surface is tapered at substantially the same rate as said first side surface and said fourth side surface is tapered at substantially the same rate as said second side surface.

10. The intraluminal device of claim 6, wherein said bend has a first opposing side surface and a second opposing side surface, said first and second opposing side surfaces extending parallel to a longitudinal axis of said intraluminal device, said first and second opposing side surfaces being adapted to abut corresponding opposing side surfaces of adjacent bends when said intraluminal device is in said low profile, and wherein a reinforcing region of said bend is formed between said first and second opposing side surfaces.

11. The intraluminal device of claim 10, further comprising a radial opening extending through said reinforcement region.

* * * * *

UNITED STATES PATENT AND TRADEMARK OFFICE
CERTIFICATE OF CORRECTION

| | | |
|---|---|---|
| PATENT NO. | : 7,753,948 B2 | Page 1 of 1 |
| APPLICATION NO. | : 11/455274 | |
| DATED | : July 13, 2010 | |
| INVENTOR(S) | : Blayne A. Roeder et al. | |

It is certified that error appears in the above-identified patent and that said Letters Patent is hereby corrected as shown below:

In the Claims

In column 7, claim 1, line 41, immediately after "and said second end portion" replace "," with --;--.

Signed and Sealed this

Twelfth Day of October, 2010

David J. Kappos
*Director of the United States Patent and Trademark Office*